United States Patent
Ellis

(10) Patent No.: US 7,124,030 B2
(45) Date of Patent: Oct. 17, 2006

(54) MUD GAS ISOTOPE LOGGING INTERPRETIVE METHOD IN OIL AND GAS DRILLING OPERATIONS

(76) Inventor: Leroy Ellis, 206 Hyde Park Dr., Richardson, TX (US) 75080

( * ) Notice: Subject to any disclaimer, the term of this patent is extended or adjusted under 35 U.S.C. 154(b) by 0 days.

(21) Appl. No.: 10/845,743

(22) Filed: May 14, 2004

(65) Prior Publication Data

US 2005/0256646 A1 Nov. 17, 2005

(51) Int. Cl.
*G01V 9/00* (2006.01)

(52) U.S. Cl. .............................................. 702/9; 702/13

(58) Field of Classification Search .................. 702/12, 702/13, 9
See application file for complete search history.

(56) References Cited

U.S. PATENT DOCUMENTS

| | | | | |
|---|---|---|---|---|
| 4,635,735 A * | 1/1987 | Crownover | ................... | 175/48 |
| 4,833,915 A * | 5/1989 | Radd et al. | ............... | 73/152.04 |
| 5,388,456 A * | 2/1995 | Kettel | ..................... | 73/152.02 |
| 6,670,605 B1 * | 12/2003 | Storm et al. | ................. | 250/255 |
| 6,888,127 B1 * | 5/2005 | Jones et al. | ............... | 250/269.1 |
| 2003/0160164 A1 * | 8/2003 | Jones et al. | ............... | 250/269.1 |
| 2004/0014223 A1 * | 1/2004 | Audibert et al. | ............... | 436/30 |
| 2004/0164237 A1 * | 8/2004 | Jones et al. | ............... | 250/269.1 |
| 2005/0099618 A1 * | 5/2005 | DiFoggio et al. | ............. | 356/70 |

OTHER PUBLICATIONS

U.S. Appl. No. 60/518,965, DiFoggio et al.*

* cited by examiner

*Primary Examiner*—Donald McElheny, Jr.
(74) *Attorney, Agent, or Firm*—Michael L. Diaz

(57) ABSTRACT

A method of interpreting mud gas samples in a drilling operation of a target area. The method starts with obtaining a plurality of mud gas samples at a plurality of incremental depths of the target area. The plurality of mud gas samples are analyzed to find various isotopic data at each depth. The isotopic data of the mud gas samples are plotting on several charts to provide a visual representation of the isotopic data trends. The charts may include: depth versus ethane/methane; depth versus $\delta^{13}C$ per mil; and depth versus $\delta^{13}C$ and gas show. In addition, the percentage methane versus $\delta^{13}C$ is provided on a separate chart. This percentage methane versus $\delta^{13}C$ chart provides engineering and geological information such as the location of lithological hydrocarbon seals, barriers, and zones of good hydrocarbon communication (e.g., compartments). This engineering and geological information is then correlated with the other charts.

26 Claims, 8 Drawing Sheets

| Sample | Depth (ft) | Total Gas (Rig. units) | Total HC (Lab. vol%) | %C1 | %C2 | %C3 | %IC4 | %NC4 | %IC5 | %NC5 | %C6+ | Dryness %C1/Cn | Wetness %C2/Cn | δ"C1 | δ"C2 | δ"C3 |
|---|---|---|---|---|---|---|---|---|---|---|---|---|---|---|---|---|
| 32897 | 2150 |   | 0.22 | 0.21 |   |   |   |   |   |   |   | 97.54 |   | -58.6 |   |   |
| 32898 | 2300 |   | 0.26 | 0.26 |   |   |   |   |   |   |   | 100 |   | -52.0 |   |   |
| 32899 | 2450 | 19 | 0.99 | 0.97 | 0.014 | 0.001 |   | 0.001 | 0.001 | 0.002 |   | 98.26 | 1.42 | -45.1 |   |   |
| 32900 | 2600 |   | 1.10 | 1.08 | 0.012 |   |   |   |   |   |   | 98.19 | 1.09 | -44.1 |   |   |
| 32901 | 2750 | 65 | 0.89 | 0.87 | 0.007 |   |   |   |   |   |   | 98.13 | 0.82 | -46.6 |   |   |
| 32902 | 2900 |   | 0.01 | 0.01 |   |   |   |   |   |   |   |   |   |   |   |   |
| 32903 | 3050 |   | 1.15 | 1.13 | 0.011 | 0.002 | 0.001 | 0.001 | 0.001 | 0.001 |   | 98.42 | 0.96 | -48.4 |   |   |
| 32904 | 3200 | 136 | 2.19 | 2.16 | 0.018 | 0.006 | 0.002 | 0.001 |   |   |   | 98.79 | 0.82 | -49.2 |   |   |
| 32905 | 3350 |   | 0.79 | 0.79 | 0.003 | 0.004 | 0.001 |   |   |   |   | 99.61 | 0.39 | -49.0 |   |   |
| 32906 | 3500 |   | 0.65 | 0.65 | 0.003 |   |   |   |   |   |   | 99.49 | 0.51 | -48.2 |   |   |
| 32907 | 3650 | 54 | 0.83 | 0.82 | 0.008 | 0.004 | 0.001 |   |   |   |   | 98.62 | 1.00 | -47.3 |   |   |
| 32908 | 3800 |   | 0.36 | 0.35 | 0.006 | 0.002 |   |   |   |   |   | 96.77 | 1.58 | -46.6 |   |   |
| 32909 | 3950 |   | 0.82 | 0.78 | 0.024 | 0.003 | 0.002 | 0.001 | 0.001 | 0.001 |   | 94.58 | 2.91 | -44.7 |   |   |
| 32910 | 4100 |   | 0.91 | 0.85 | 0.031 | 0.013 | 0.003 | 0.002 | 0.002 | 0.002 |   | 93.51 | 3.41 | -44.4 |   |   |
| 32911 | 4250 |   | 0.97 | 0.87 | 0.051 | 0.020 | 0.006 | 0.005 | 0.005 | 0.005 |   | 90.00 | 5.28 | -41.6 |   |   |
| 32912 | 4293 | 550 | 7.73 | 6.71 | 0.470 | 0.280 | 0.071 | 0.061 | 0.061 | 0.074 |   | 86.84 | 6.03 | -42.0 | -34.7 | -33.1 |
| 32913 | 4311 | 760 | 9.81 | 8.59 | 0.600 | 0.340 | 0.081 | 0.063 | 0.063 | 0.070 |   | 87.59 | 6.42 | -42.0 |   |   |
| 32914 | 4326 | 120 | 1.30 | 1.16 | 0.071 | 0.038 | 0.010 | 0.008 | 0.008 | 0.010 |   | 88.00 | 5.44 | -42.2 |   |   |
| 32915 | 4360 | 200 | 2.44 | 2.14 | 0.140 | 0.081 | 0.019 | 0.018 | 0.018 | 0.021 |   | 87.81 | 5.74 | -42.1 |   |   |
| 32916 | 4423 | 125 | 1.42 | 1.24 | 0.086 | 0.047 | 0.011 | 0.010 | 0.010 | 0.012 |   | 87.57 | 5.07 | -41.9 |   |   |
| 32917 | 4514 | 700 | 13.41 | 12.6 | 0.430 | 0.220 | 0.037 | 0.025 | 0.025 | 0.030 |   | 94.28 | 3.21 | -42.5 | -33.7 | -32.7 |
| 32918 | 4565 | 390 | 4.57 | 3.97 | 0.280 | 0.100 | 0.037 | 0.029 | 0.029 | 0.034 |   | 86.89 | 6.13 | -41.6 |   |   |
| 32919 | 4576 | 850 | 11.16 | 9.91 | 0.610 | 0.400 | 0.077 | 0.053 | 0.053 | 0.059 |   | 88.78 | 5.46 | -42.9 | -34.0 | -32.9 |
| 32920 | 4600 | 220 | 2.38 | 2.11 | 0.140 | 0.080 | 0.015 | 0.011 | 0.011 | 0.014 |   | 88.62 | 5.88 | -42.4 |   |   |
| 32921 | 4650 |   | 1.58 | 1.40 | 0.091 | 0.059 | 0.019 | 0.009 | 0.009 | 0.012 |   | 88.43 | 5.75 | -42.6 |   |   |
| 32922 | 4700 |   | 2.61 | 2.33 | 0.140 | 0.078 | 0.015 | 0.014 | 0.014 | 0.018 |   | 89.34 | 5.37 | -42.8 | -33.5 | -32.5 |
| 32923 | 4714 | 1700 | 45.61 | 43.2 | 1.530 | 0.350 | 0.100 | 0.046 | 0.046 | 0.041 |   | 94.71 | 3.35 | -43.9 |   |   |
| 32924 | 4900 | 140 | 1.93 | 1.78 | 0.089 | 0.033 | 0.008 | 0.006 | 0.006 | 0.007 |   | 92.32 | 4.62 | -43.8 |   |   |
| 32925 | 5050 |   | 0.30 | 0.27 | 0.014 | 0.005 | 0.002 | 0.003 | 0.003 | 0.004 |   | 89.79 | 4.66 | -44.2 |   |   |

*FIG. 2A*

| | | | | | | | | | | | |
|---|---|---|---|---|---|---|---|---|---|---|---|
| 32927 | 5350 | | 1.19 | 1.15 | 0.024 | 0.007 | | | | | |
| 32928 | 5500 | | 1.21 | 1.17 | 0.025 | 0.008 | 0.001 | | | 96.73 | 2.02 | -46.9 |
| 32929 | 5650 | | 1.38 | 1.33 | 0.033 | 0.012 | 0.002 | 0.002 | 0.003 | 96.60 | 2.06 | -48.0 |
| 32930 | 5800 | 80 | 0.98 | 0.94 | 0.030 | 0.013 | 0.002 | 0.002 | 0.003 | 96.73 | 2.40 | -48.1 |
| 32931 | 5950 | 80 | 0.95 | 0.89 | 0.037 | 0.017 | 0.001 | | | 95.54 | 3.05 | -48.4 |
| 32932 | 6100 | 60 | 1.44 | 1.32 | 0.074 | 0.039 | 0.001 | | | 94.06 | 3.91 | -48.5 |
| 32933 | 6250 | | 0.80 | 0.73 | 0.039 | 0.023 | 0.004 | 0.002 | 0.001 | 91.53 | 5.13 | -48.4 |
| 32934 | 6400 | 92 | 1.10 | 0.96 | 0.074 | 0.048 | 0.003 | 0.002 | 0.001 | 91.11 | 4.87 | -47.6 |
| 32935 | 6550 | 42 | 0.72 | 0.62 | 0.047 | 0.033 | 0.007 | 0.005 | 0.002 | 87.02 | 6.71 | -48.8 |
| 32936 | 6700 | | 1.16 | 1.02 | 0.078 | 0.047 | 0.004 | 0.004 | 0.005 | 86.65 | 6.57 | -48.4 |
| 32937 | 6850 | | 0.83 | 0.72 | 0.060 | 0.037 | 0.006 | 0.004 | 0.004 | 87.83 | 6.72 | -48.9 |
| | | | | | | | 0.004 | 0.003 | 0.003 | 86.67 | 7.22 | -48.7 |

*FIG. 2B*

MUD GAS ISOTOPE LOGGING INTERPRETIVE METHOD IN OIL AND GAS DRILLING OPERATIONS

BACKGROUND OF THE INVENTION

1. Technical Field of the Invention

This invention relates to isotopic analysis associated with oil and gas drilling operations and, more particularly, to an interpretive method of a novel mud gas isotope logging technique.

2. Description of Related Art

Within the oil and gas industry, laboratory analysis of gas samples obtained during a drilling operation can be employed to determine geochemical information associated with strikes of oil or gas deposits. The laboratory analysis may include the acquisition of compositional and isotopic data of sampled subsurface gases. The data is applied to traditional geochemical plots and templates as contained in scientific literature. The interpretation of this data is used to provide geochemical information on where the gas provenance may have originated from ("source rock"), how thermally mature the gas is (how hot the source got before expelling gas), whether subsurface post-generation effects (pressure, volume, temperature (PVT) effects, biodegration, water-washing, etc.) were encountered during migration of the gas from the source rock to a reservoir, and any problems or effects the hydrocarbons in the reservoir subsequently experienced.

Existing well sampling techniques use physical gas samples for compositional and isotopic laboratory analysis. There are typically three ways that gas samples may be obtained. First, gas can be sampled directly from the reservoir formation of interest using a logging tool, such as a modular dynamic tester (MDT) or a repeat formation tester (RFT). To use these logging tools, the entire drill bit and string (tubing) has to be removed before the logging tools can be sent back down to the formation interval of interest in order to obtain a physical sample. Since drilling operations must be stopped while using these logging tools, the logging tools are used sparingly and limited sample numbers are collected due to the expense incurred in delaying drilling operations. Another way to obtain gas samples is by "canned cuttings." Rock samples ("cuttings"), representative of a subsurface formation, are pulverized by a drill bit as the bit penetrates rock strata. The rock samples are then collected in sealed cans upon return to the surface in the circulating mud stream where the cuttings are able to "degas." Gases accumulating in the sealed cans can then be analyzed in a laboratory as "headspace gases." The cuttings are collected/suspended in the mud stream that is continuously circulated around the drill bit during drilling. The mud stream is employed to help lubricate and cool the drill bit and prevent rock material from accumulating and collecting around the drill bit. Because the cuttings vary in size and density according to the rock material being drilled and type of drill bit, the heavier and more dense material is likely to sink below smaller, less dense material as the mud is circulated up to the surface. Therefore, these cuttings "smear" in the mudstream as they circulate toward the surface. To compensate for this, canned cuttings are usually collected over a large depth interval (typically ninety feet) in an attempt to collect as representative a sample as possible. The third way that a sample is collected is by directly sampling gases entrained in the mud system during drilling. As a well drill bit penetrates and pulverizes rock material in its path, free and absorbed gases entrained in the pulverized rock and immediately adjacent rock formation (side of the borehole) flow into the mud stream as it circulates around the drill bit. These gases are carried to the surface and collected as they exsolve/degas from the returning mud stream.

Standard mud gas chromatographic compositional analyses and interpretations suffer from several disadvantages. None of the analyses effectively detail or correlate geological information such as seals and barriers (hydrocarbon communication and compartmentalization problems), good communication zones, or gas diffusion into their interpretation. Data can result in false positives and negatives where changes in operational drilling conditions related to variables such as increased rate of penetration (ROP) or mud weight increases occur. A more advanced method is needed which employs an integrated interpretation and approach of drilling, geological and engineering information together with mud-gas chromatographic compositional and isotopic analysis.

Typically, existing methods merely employ geochemical data to provide geochemical interpretations. The present invention employs geochemical data to provide geochemical, geological and engineering interpretations and solutions.

Thus, it would be a distinct advantage to have an interpretive method of analysis of mud-gas samples utilizing chromatographic compositional and isotopic analysis concomitant with a geochemical, geological, and engineering interpretation applied to the data. It is an object of the present invention to provide such an interpretative method specific to mud gas isotope logging.

SUMMARY OF THE INVENTION

In one aspect, the present invention is a novel method of interpreting geological and engineering information from mud gas samples in a drilling operation of a target area. The method begins by profiling sampled gases at incremental depths during drilling. Sampled gases are analyzed to obtain compositional and isotopic data on the gas samples. Next, the isotopic and compositional data are plotted on charts. Specific new methods of interpretation are employed to interpret the data in relation to geochemical, geological and engineering issues surrounding oil and gas exploration and production. Geochemical, geological, and engineering information are derived or divined from the plotted data.

In another aspect, the present invention is a new method of interpreting gas samples in a drilling operation in a target area. The method first begins by obtaining gas samples at incremental depths during drilling. Next, data is obtained from analysis of all gas samples collectively. A chart is then created from the isotopic data providing a representation of percentage methane versus an isotopic value. Geological information, such as the location of barriers, seals and zones of good communication are then obtained from this chart.

In still another aspect, the present invention is a method of interpreting gas samples in a drilling operation of a target area. The method begins by obtaining gas samples at incremental depths during drilling. Next, the gas samples are analyzed to obtain isotopic data. The isotopic data includes data associated with a composition of ethane and methane within each of the gas samples. The isotopic data is plotted on a first chart and a second chart. The first chart illustrates percentage methane versus an isotopic value. The second chart illustrates methane values at each incremental depth. Next, geological information is determined from the first chart. The determined geological information from the first chart is then correlated with the second chart.

BRIEF DESCRIPTION OF THE DRAWINGS

The invention will be better understood and its numerous objects and advantages will become more apparent to those skilled in the art by reference to the following drawings, in conjunction with the accompanying specification, in which:

FIG. 2 is a table illustrating typical collective tabulated data revealing mud gas composition and mud gas isotope sampling data for an exemplary drilling site;

DETAILED DESCRIPTION OF EMBODIMENTS

Figure 1:
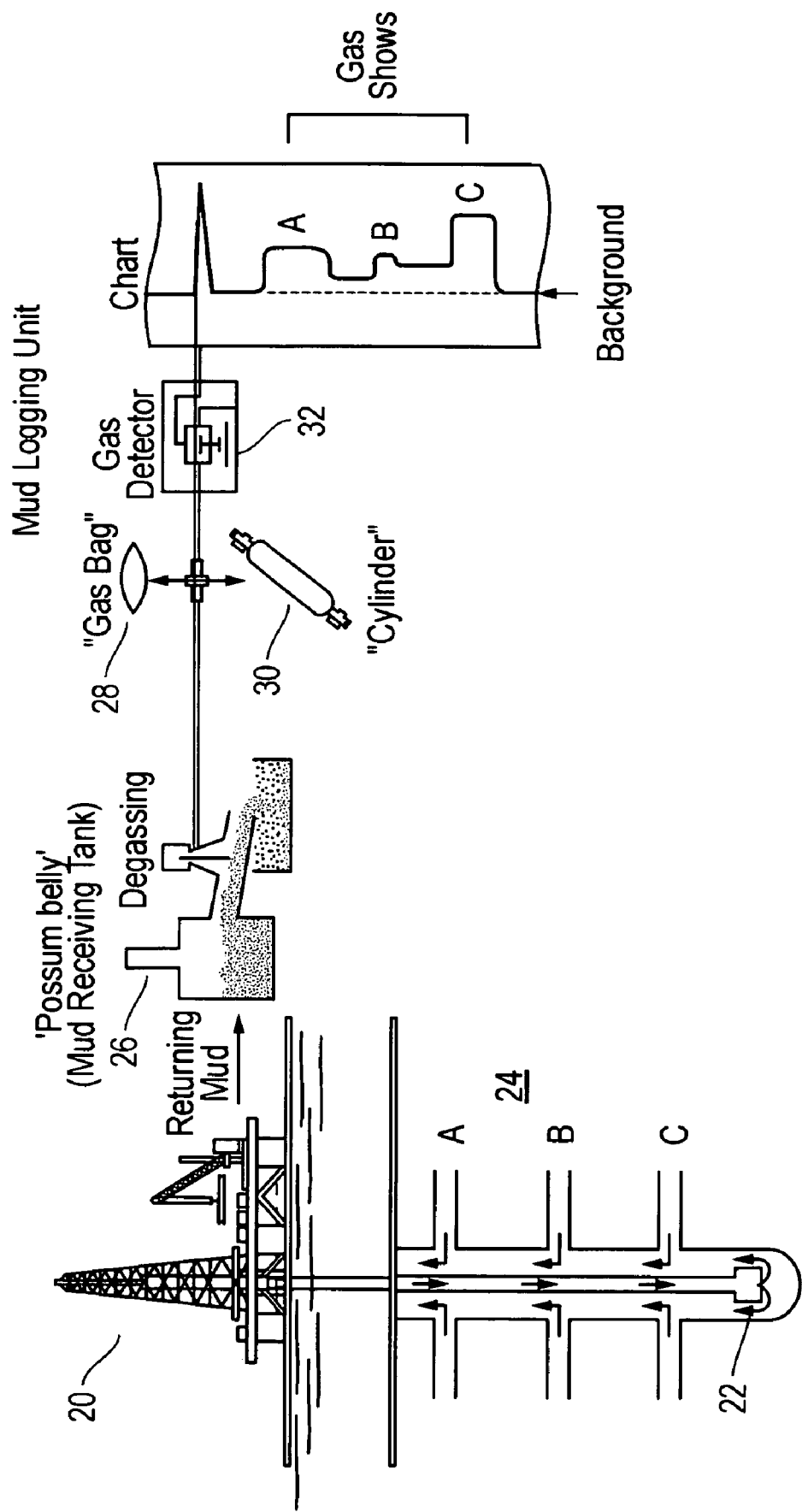
FIG. 1 is block diagram illustrating principles of mud circulation during drilling operations and sampling of mud gases in the preferred embodiment of the present invention.

The present invention is a new, specific and enhanced interpretive method of a recently introduced technique termed mud gas isotope logging. FIG. 1 is block diagram illustrating principles of mud circulation during drilling operations and sampling of mud gases in the preferred embodiment of the present invention. A well 20 having a drill 22 drills down into the ground 24. Levels A, B, and C provide exemplary gas shows related to subsurface reservoirs. Mud is circulated around the drill 22 to provide lubrication for the drill and removing debris (cuttings) as it drills. The mud is circulated to the surface. The returning mud is collected on the surface within a mud receiving tank 26, also known as a possum belly. The gas is degassed/exsolved from the mud and collected within a gas sampling device 28, a cylinder 30, or through a mobile/onsite/in-situ isotopic analyzer 31. Typically, at a laboratory or mud logging unit, a gas detector 32 (such as a gas. chromatograph or mass spectrometer) is utilized to measure isotopic and compositional ratios of different hydrocarbon species. All the hardware used in the present invention is currently used in the existing interpretive process.

Mud gas samples provide much more reliable and accurate methane and ethane isotopic data for the interpretive process than other mud-based methods. Because of inherent inaccuracies in canned cuttings, especially with methane and ethane hydrocarbons, canned cuttings are not effectively used in the present invention. Canned cutting samples suffer from a known error relating to an isotopic fractionation effect with the methane and to some extent the ethane gases. Since methane data is predominately employed within the present invention, canned cuttings are not acceptable. Additionally, canned cuttings are typically collected over larger composite depth intervals and, thus, show an averaged "smear" effect with isotopic values resulting from exposure to various sedimentary rock intervals throughout that range. The mud gas isotopic analysis of the present invention typically involves more depth-specific and accurate "non-averaged" data than found with canned cuttings. In the preferred embodiment of the present invention, for a frontier basin/new field wildcat well, the samples are taken at regular depths (e.g., every 150–500 feet), in shallow intervals in order to establish a background trend, and every 10–30 feet in oil and gas show intervals. Once a background is established in a field, the spacing may be relaxed to a 500 foot or greater interval on later wells as more experience and knowledge is gained in the area. Additionally, gas samples collected in gas sampling devices typically see more restricted gas diffusion in the mud stream on the way to the surface. Therefore, the sample depth recorded for the gas bag samples is considered to more closely approximate the actual depth, whereas canned cuttings by nature may not accurately indicate the actual depth as rock density and fractal variables come into play.

The raw data received from the gas samples are preferably tabulated. FIG. 2 is a table illustrating tabulated data of a typical mud gas composition and gas isotope sampling data for an exemplary drilling well. As stated above, samples are taken at regular intervals through the well. The gas composition data and carbon isotope data may be arranged in any fashion. As illustrated in FIG. 2, matching rows are characterized by depth of the samples.

Figure 3:
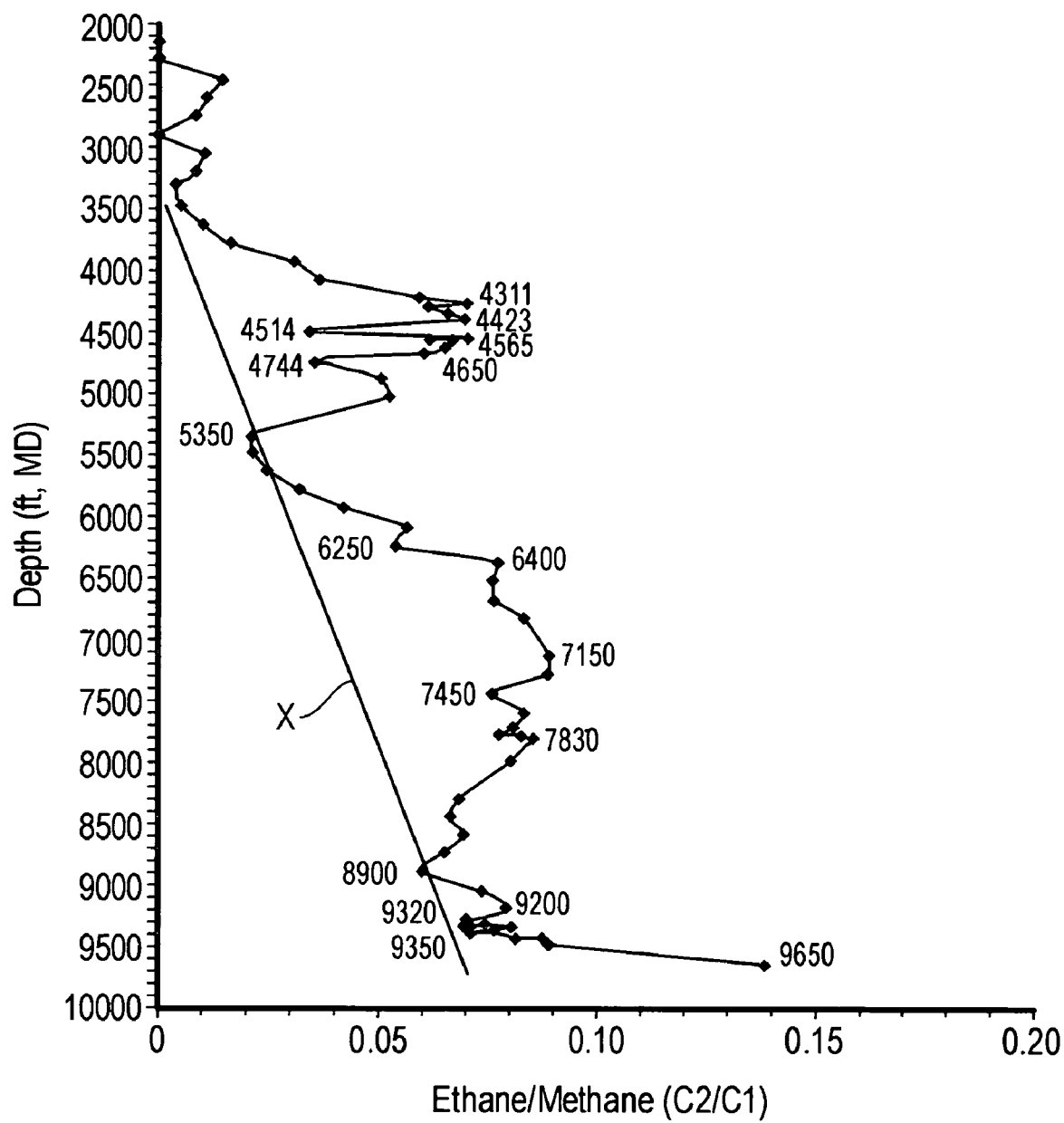
FIG. 3 is a depth versus ethane/methane (C2/C1) chart derived from tabulated data in FIG. 2.

FIG. 3 is a depth versus ethane/methane (C2/C1) chart derived from tabulated data in FIG. 2. The tabulated data from FIG. 2 is used to plot ethane/methane points (X-axis) versus depth (Y-axis). The objective of FIG. 3 is to observe any high C2/C1 ratios (i.e., gas wetness). High ratios are generally those having a value over approximately 0.1. Values over 0.1 or any relatively high value in a data set may suggest a wet gas that may be associated with hydrocarbon fluids, such as oil.

Figure 4:
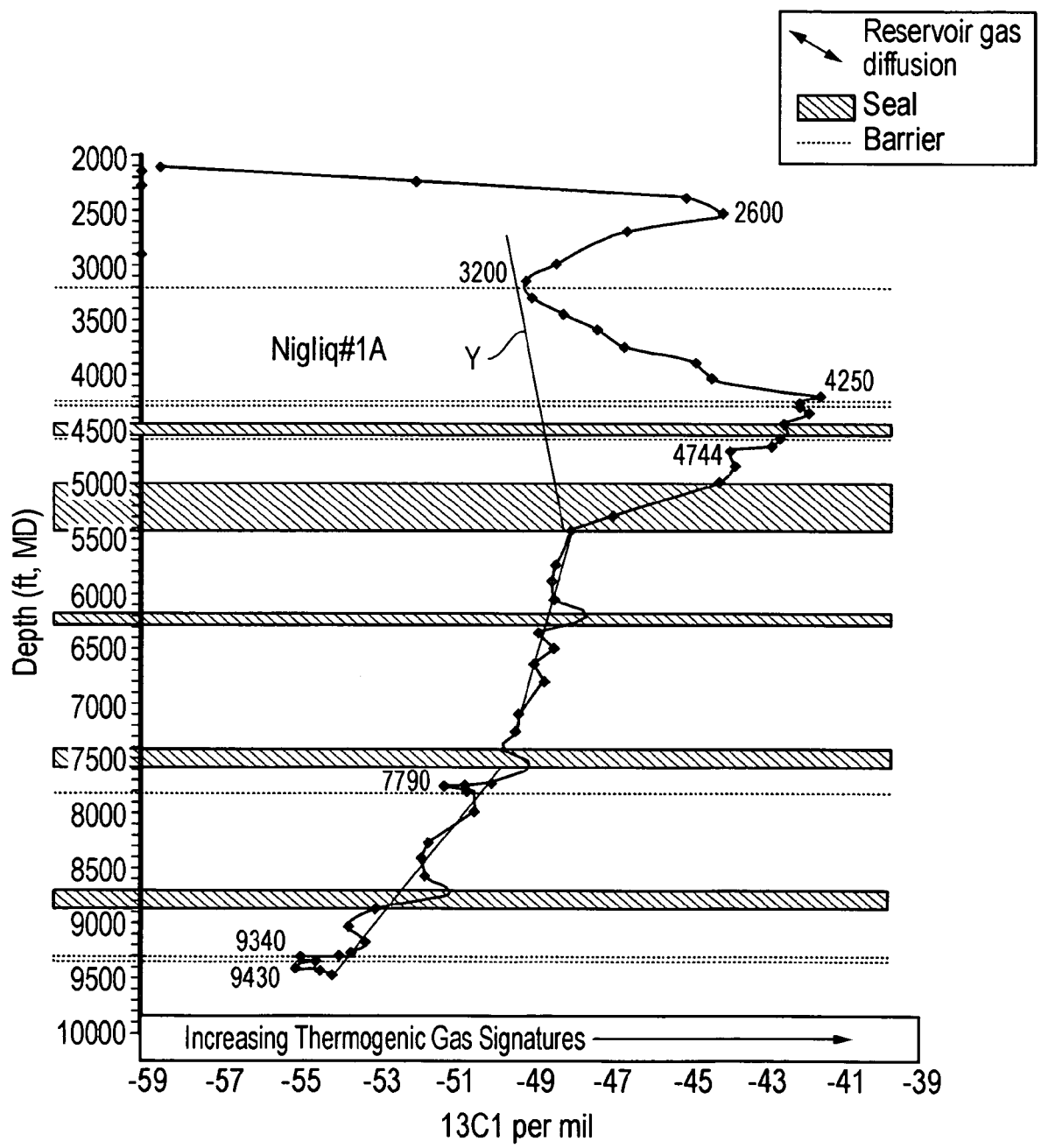
FIG. 4 is a depth versus isotopic data chart derived from tabulated data in FIG. 2.

One of the novel features in the interpretive methodology of the present invention is the determination of a methane isotopic background trend in an oil and gas drilling well (FIG. 4). Still referring to FIG. 3, a wetness background trend is similarly plotted as a background trend line X. Mud gases released at the surface from the drilling mud form mixtures of predominantly hydrocarbon gases and air. The concentrations of sampled mud gases vary considerably and may show hydrocarbon concentrations close to 0 vol % or as high as 90 vol %.

Depending on individual well mud weighting protocols, typical background trend levels are reflected by hydrocarbon gas concentrations between 0.01 vol % and 1 vol %, while hydrocarbon gas concentrations greater than 2 vol % are generally characteristic of gas shows.

In contrast, gas samples from wireline samplers or production tests are usually uncontaminated by atmospheric gases, so hydrocarbon concentrations are usually quite high.

Any high or low C2/C1 ratios can only be accurately ascertained after the background is considered. Therefore, the background is plotted on FIG. 3 to assist in accurate analysis of the data permitting integration and correlations with similar isotopic trends and shows as revealed in subsequent figures and steps of the interpretive process.

FIG. 4 is a depth versus isotopic data (e.g., $\delta^{13}C$, $\delta^2H$) chart derived from tabulated data in FIG. 2. FIG. 4 is used to plot interpolated isotopic data (e.g., methane)(x-axis) against depth (Y-axis). Relatively heavy isotopic (less negative) and light isotopic (more negative) values are observed. Isotopically heavy values may suggest migrated thermogenic petroleum hydrocarbons. These heavy and light isotopic features are typically better revealed when a background line Y is plotted. Again, this background trend is interpreted, observed and plotted on FIG. 4 in a similar manner as discussed in FIG. 3. The identified seals and barriers shown in FIG. 4 are not determined until after conclusion from FIG. 6 as discussed below. Identification of any known or identified reservoir depth interval may also be shown on FIG. 4 to assist in identifying isotopic shows. If not specified, the depth intervals highlighted are those that encompass the highest gas shows and C2/C1 ratios identified in FIGS. 3 and 5 discussed below. In another aspect of the present invention, a broad isotopic peak/profile registered as a deviation from the background trend may suggest gas diffusion as indicated in FIG. 4.

Figure 5:
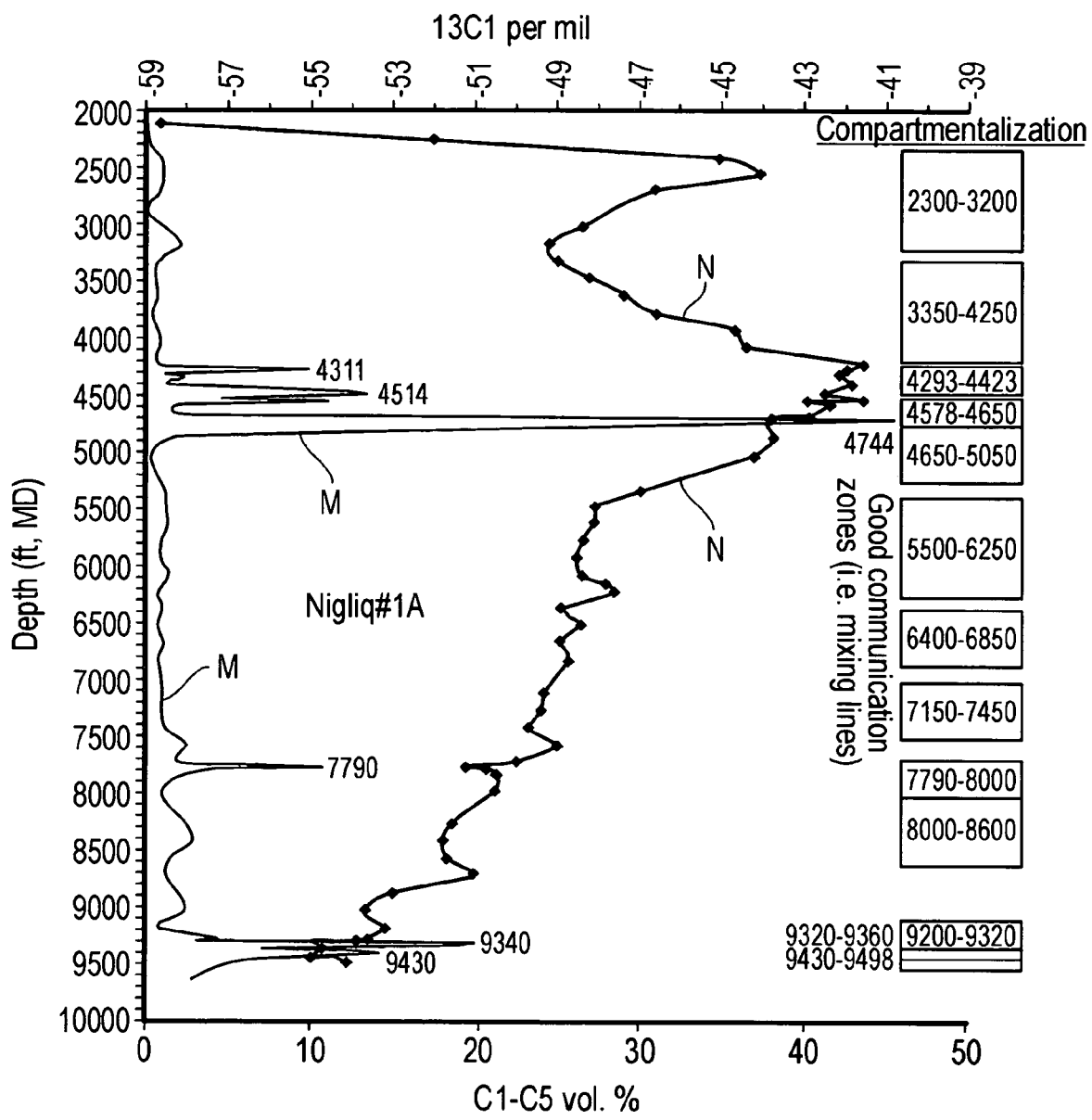
FIG. 5 is a depth versus isotopic data and gas show chart derived from tabulated data in FIG. 2.

FIG. 5 is a depth versus isotopic data and gas show chart derived from tabulated data in FIG. 2. Isotopic data and gas show (sum of all measured hydrocarbon gas concentrations) are both illustrated as a double x-axis plot. High gas shows are identified in FIG. 5 as data set M, while isotopic shows are shown as data set N. The plot and interpretive process enable an analyst to determine if any high gas shows coincide with any isotopic shows. Good communications zones (compartments) shown in FIG. 5 are where hydrocarbons are mixing and derived from FIG. 6 as part of the new interpretive process. The chart may include annotations of depths labeled for the highest values (gas shows). Although not shown, a background line for the isotopic trend may also be plotted on FIG. 5 as interpreted in FIG. 4. Additionally, annotation may be used to identify any identified reservoir depth intervals. If not specified, the depth intervals inferred are those that encompass the highest gas shows and corresponding C2/C1 ratios. The good communications zones (compartments), determined in FIG. 6, may be shown in FIG. 5.

Figure 6:
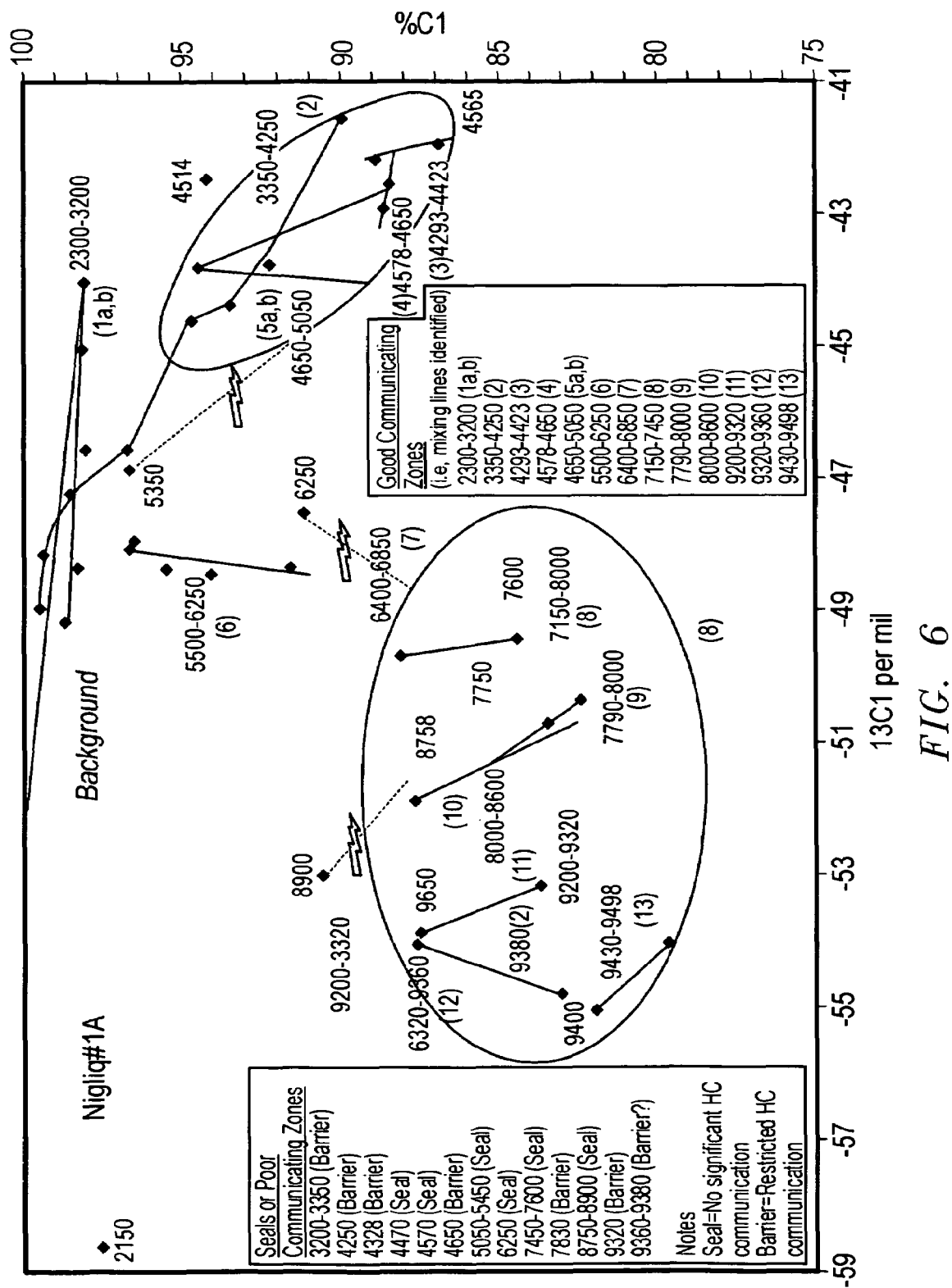
FIG. 6 illustrates a percentage C1 normalized to all other measured HC gases (i.e., C1 through C6) versus isotopic data chart in the preferred embodiment of the present invention.

Another new and novel aspect of the interpretative methodology of the present invention is shown in FIG. 6. FIG. 6 illustrates a normalized percentage C1 versus isotopic data (e.g., $\delta^{13}C$, $*^2H$) chart in the preferred embodiment of the present invention. Percentage C1 is illustrated on the Y-axis and isotopic data is displayed on the x-axis. Straight lines (which usually are defined by at least three sequential depth data points) or other identified trends within the data are then identified and known as "mixing lines." These mixing lines equate to good subsurface zones (compartments) in hydrocarbon gas communication. The points where the mixing lines start and end typically reveal "breaks" which may equate to lithological hydrocarbon communication seals or barriers. Barriers typically occur where a simple break in a mixing line occurs. Seals typically occur where the break is significant and the next depth data point deviates substantially. Either the next mixing line reverses direction or the next data point is far removed from the previous depth data point or mixing line. The data which are identified as mixing lines and seals/barriers are tabulated and may be plotted on FIGS. 4 and 5. FIG. 6 may include depth range labeling for any mixing line. Additionally, straight line-of-best-fit may also be drawn for data approximating a mixing line. Data groups that are tightly clustered are similarly interpreted to indicate good communication zones, analogous to mixing lines. Typically, background data include those data points that fall along backgrounds observed on an isotopic data plot (FIG. 4) and, in most cases, forms a general trend (typically a slope) towards the bottom right of the plot. Referring back to FIG. 4, the lithological hydrocarbon seals and barrier determined in FIG. 6 are applied and annotated to FIG. 4. Additionally, referring to FIG. 5, the zones of good hydrocarbon communication (compartments) are applied and annotated to FIG. 5, as derived from FIG. 6.

Figure 7:
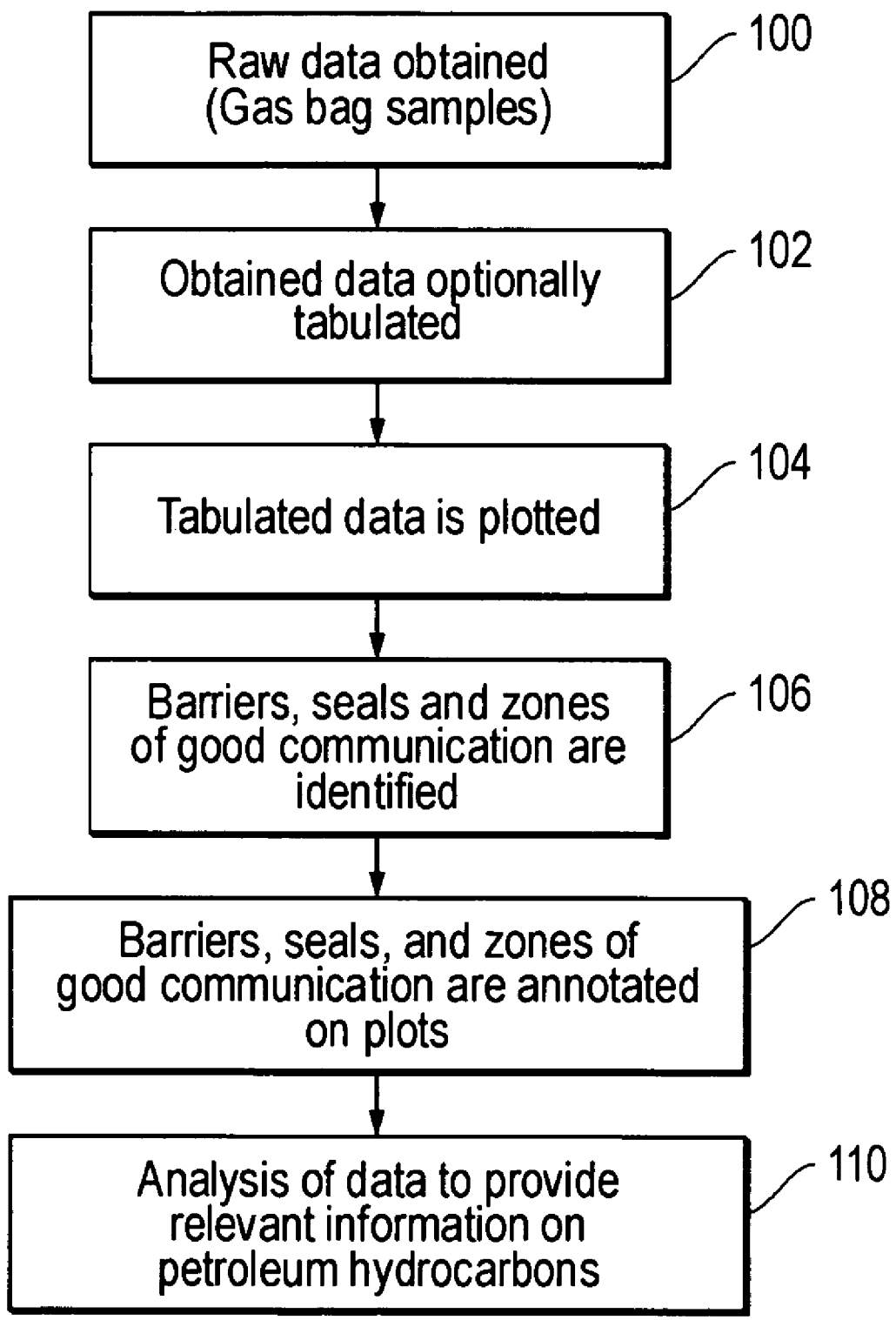
FIG. 7 is a flow chart outlining the specific steps required for interpreting mud gas isotope logging according to the teachings of the present invention.

FIG. 7 is a flow chart outlining the steps for interpreting engineering and geological interpretations from data determined from mud gas isotope logging according to the teachings of the present invention. With reference to FIGS. 1–7, the steps of the method will now be explained. The method begins with step 100, where data is obtained. Data is obtained from gas samples of mud taken at regular sequential depth intervals. In alternate embodiments of the present invention, the interval may be varied according to the subsurface lithologies encountered. However, in any sample logging using the mud gas isotope logging technique, samples must be obtained at sufficiently frequent intervals to determine a background trend, which may vary as depth increases or geological environments determine. The gas bag samples are analyzed to provide gas compositional data and carbon isotopic data. Next, in step 102, the data is optionally tabulated and specific ratios determined or calculated. The raw data and constructed ratios may alternatively be directly plotted to the desired plots as required, without tabulating the collected data. However, in the preferred embodiment of the present invention, the data is tabulated for organization in order to facilitate the compositional and isotopic ratios required for the data interpretation.

Next, in step 104, the raw data obtained in step 100 and tabulated in step 102 is plotted as required. One of the plots may include a depth versus C2/C1 chart (FIG. 3), a depth versus isotopic data per mil chart (FIG. 4), and a depth versus isotopic data and gas show chart (FIG. 5). Each of these charts (FIGS. 4 and 5) preferably includes background trend lines to distinguish high and low ratios. It should be noted that gas samples are taken at specific depth intervals because background trends are not static, but rather may change with depth and subsurface geological environment. Essential to this technique, a percentage of C1 versus isotopic data chart (FIG. 6) is employed.

Next in step 106, barriers, seals and zones of good hydrocarbon communications (compartments) are determined. FIG. 6 is specifically used to identify mixing lines which are indicative of good hydrocarbon communication zones (compartments). The start and end of each mixing line typically reveals breaks which equate to seals or barriers. A barrier occurs where a simple break between mixing lines occurs. A seal occurs where the break is significant and the next depth data point or mixing line deviates substantially. The next mixing line either reverses direction or the next data point is far removed from the previous point or mixing line. The method then moves to step 108 where the barriers, seals, and good hydrocarbon communication zones (compartments) are annotated on the plots (FIGS. 3, 4, and 5).

Next, in step 110, areas indicative of gas/oil are identified. These noteworthy areas are determined by background contrasting isotopic values associated with good hydrocarbon communication zones. Thus, significant geological characteristics are applied to geochemical analysis to provide accurate analysis during drilling operations.

The present invention provides many advantages which currently are not available in existing analytical and interpretive techniques. The present invention provides detailed downhole isotopic logging and delivers to the geoscientist unparalleled geochemical perspective on the drilling and engineering operation, geological environment and hydrocarbon charging/filling history. Specifically, the present invention incorporates analysis of relevant geological data into geochemical analysis to reveal drilling characteristics and other operations that are important in determining significant areas of interest in regards to petroleum hydrocarbons. Additionally, the present invention takes background trends, which are not static, into account in identifying and interpreting significant hydrocarbon shows of a sampled area.

It is thus believed that the operation and construction of the present invention will be apparent from the foregoing description. While the method shown and described has been characterized as being preferred, it will be readily apparent that various changes and modifications could be made therein without departing from the scope of the invention as defined in the following claims.

What is claimed is:

1. A method of interpreting sampled mud gas compositional and isotopic data in a drilling operation of a target area, said method comprising the steps of:
profiling a plurality of mud gas samples through a well bore at a plurality of incremental depths of the well bore;
analyzing the plurality of gas samples to obtain a plurality of isotopic data points associated with hydrocarbon isotopic composition of the plurality of gas samples, the plurality of isotopic data points includes data associated with a composition of ethane and methane within each of the mud gas samples;
plotting the plurality of isotopic data points;
determining geological information from the target area derived from the plotted plurality of isotopic data points; and
analyzing the plurality of isotopic data points to geochemically interpret the geological information.

2. The method of interpreting gas samples of claim 1 wherein the geological information includes information on seals, barriers, good communication zones, or gas diffusion within the target area.

3. The method of interpreting mud gas samples of claim 1 wherein the step of plotting the plurality of isotopic data points includes plotting the plurality of isotopic data points on at least one chart, the one chart providing a visual representation of the isotopic data points.

4. The method of interpreting mud gas samples of claim 3 wherein the step of plotting the plurality of isotopic data points includes:
determining isotopic background at each incremental depth of the target area;
determining a background trend from the isotopic background; and
plotting the background trend on the chart.

5. The method of interpreting mud gas samples of claim 4 wherein at least one chart is associated with an ethane/methane ratio at each incremental depth.

6. The method of interpreting mud gas samples of claim 4 wherein at least one chart is associated with isotopic composition of the plurality of mud gas samples.

7. The method of interpreting mud gas samples of claim 4 wherein at least one chart is associated with a ratio of ethane and methane within each mud gas sample.

8. The method of interpreting mud gas samples of claim 4 wherein at least one chart includes a representation of percentage methane versus isotopic composition.

9. The method of interpreting mud gas samples of claim 8 wherein the chart providing a representation of percentage of methane versus isotopic data provides a geological indicator.

10. The method of interpreting mud gas samples of claim 9 wherein the geological indicator provides a location of a good hydrocarbon communication compartment located within the target area.

11. The method of interpreting mud gas samples of claim 9 wherein the geological indicator provides a location of a geological hydrocarbon communication barrier located within the target area.

12. The method of interpreting mud gas samples of claim 9 wherein the geological indicator provides a location of a geological hydrocarbon seal located within the target area.

13. The method of interpreting mud gas samples of claim 9 wherein the geological indicator is determined by data points plotted on the chart and provides at least one substantially trend indicative of a zone of good hydrocarbon communication.

14. The method of interpreting mud gas samples of claim 13 wherein a break between two substantially straight lines indicates a hydrocarbon communication barrier.

15. A method of interpreting mud gas samples in a drilling operation in a target area, said method comprising the steps of:
obtaining a plurality of mud gas samples at a plurality of incremental depths of the target area;
obtaining isotopic data from the plurality of mud gas samples, associated with hydrocarbon isotopic composition of the plurality of gas samples, the plurality of isotopic data points includes data associated with a composition of ethane and methane within each of the mud gas samples;
creating a chart from the obtained isotopic data, the chart providing a representation of percentage methane versus isotopic data; and
deriving geological information from the chart.

16. The method of interpreting mud gas samples in a drilling operation of claim 15 further including the steps of:
plotting compositional data on a second chart, the second chart providing an ethane/methane ratio at each incremental depth; and
analyzing the second chart in conjunction with the geological information from the first chart.

17. The method of interpreting mud gas samples of claim 15 wherein the geological information includes a location of at least one zone of good hydrocarbon communication located within the target area.

18. The method of interpreting mud gas samples of claim 15 wherein the geological information includes a location of at least one geological hydrocarbon barrier located within the target area.

19. The method of interpreting mud gas samples of claim 15 wherein the geological indicator is at least one geological seal located within the target area.

20. The method of interpreting mud gas samples of claim 15 wherein the geological indicator includes a visual representation on the chart providing sequential depth data points forming at least one substantially straight line indicative of a zone of good hydrocarbon communication.

21. The method of interpreting mud gas samples of claim 20 wherein a break between two substantially straight lines plotted on the chart indicates a barrier to hydrocarbon communication.

22. The method of interpreting mud gas samples of claim 15 wherein the step of creating a chart from the obtained isotopic data includes providing a representation of percentage methane versus $\delta^{13}C$.

23. A method of interpreting mud gas samples in a drilling operation of a target area, said method comprising the steps of:
obtaining a plurality of mud gas samples at a plurality of incremental depths of the target area;
analyzing the plurality of mud gas samples to obtain a plurality of isotopic data points, the plurality of isotopic data points includes data associated with a composition of ethane and methane within each of the mud gas samples;

plotting the plurality of isotopic data points to provide a visual representation on a first chart illustrating percentage methane versus isotopic data and a second chart illustrating methane values of the plurality of isotopic data points at each incremental depth;

determining geological information from the target area derived from the first chart; and correlating the determined geological information from the first chart with the second chart.

24. The method of interpreting mud gas samples in a drilling operation of claim 23 wherein the first chart provides mixing lines indicative of at least one good hydrocarbon communication zone.

25. The method of interpreting mud gas samples in a drilling operation of claim 23 further comprising the steps of:

determining a background level of isotopic values for each incremental depth; and plotting the background level on the second chart.

26. The method of interpreting mud gas samples in a drilling operation of claim 23 wherein the step of plotting the plurality of isotopic data points includes providing the first chart illustrating percentage methane versus $\delta^{13}C$.

* * * * *